United States Patent [19]

Sumner, Jr. et al.

[11] Patent Number: 5,157,102

[45] Date of Patent: Oct. 20, 1992

[54] DIOLS AND POLYESTERS MADE THEREFROM

[75] Inventors: Charles E. Sumner, Jr., Kingsport; Ernest W. Arnold, Blountville; Gary D. Boone, Johnson City, all of Tenn.

[73] Assignee: Eastman Kodak Company, Rochester, N.Y.

[21] Appl. No.: 763,840

[22] Filed: Sep. 23, 1991

[51] Int. Cl.$^5$ ............................................. C08G 63/02
[52] U.S. Cl. ..................................... 528/272; 528/271
[58] Field of Search ......................................... 528/272

[56] References Cited

PUBLICATIONS

Bethell, D. et al. "Courtaulds Research", P.O. Box 111, Lockhurst Lane, Coventry, pp. 1097-1103.
Reinking, et al., *J. Appl. Polymer Sci.*, 7, 2153 (1963).

*Primary Examiner*—John Kight, III
*Assistant Examiner*—T. Mosley
*Attorney, Agent, or Firm*—Bernard J. Graves, Jr.; William P. Heath, Jr.

[57] ABSTRACT

Provided is indeno[1,2-β] fluorene-6,12-diol, useful as an intermediate to polyesters. Also provided are derivatives of this compound and novel polyesters having residues of indeno[1,2-β] fluorene-6,12-diol or its derivatives copolymerized therein and shaped or formed articles comprised of the novel polyesters.

11 Claims, No Drawings

DIOLS AND POLYESTERS MADE THEREFROM

FIELD OF THE INVENTION

This invention relates to the field of organic chemistry. More particularly, this invention relates to indeno[1,2-$\beta$] fluorene-6,12-diol, and derivatives thereof, which are useful as intermediates to polyesters.

BACKGROUND OF THE INVENTION

Diols containing aromatic moieties are valuable as intermediates for the synthesis of polyesters. For example, bisphenol-A is known to yield polyesters having high glass transition temperatures.(See, for example, Reinking, et al., *J. Appl. Polymer Sci.*, 7, 2153 (1963).) It is generally accepted by those skilled in the art that modifications of polyesters, particularly polyethyleneterephthalate (PET), can best be accomplished by copolymerization of a diol with terephthalic acid and ethylene glycol as opposed to copolymerization of a diacid with terephthalic acid and ethylene glycol. Diols that are structurally rigid are believed to raise the glass transition temperature of the PET when copolymerized, that is, when some of the ethylene glycol is replaced with the diol. Few rigid diols are available. Examples include 2,2,4,4-tetramethylcyclobutanediol, cyclo-pentanediol, and bisphenol-A.

SUMMARY OF THE INVENTION

The present invention provides indeno[1,2-$\beta$] fluorene-6,12-diol, and derivatives thereof which are useful as intermediates to polyesters. The title compounds are prepared by reduction of the corresponding diketone. Also provided are novel polyesters comprised of residues of these compounds and shaped or formed articles comprised of the polyesters.

DETAILED DESCRIPTION OF THE INVENTION

The present invention provides compounds of formula (1)

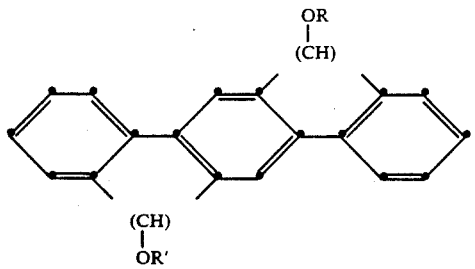

wherein R and R' are independently hydrogen or $C_1$–$C_6$ hydroxyalkyl residues.

The above compound, indeno[1,2-$\beta$] fluorene 6,12-diol, can be prepared by reduction of indeno[1,2-$\beta$]fluorine-6,12-dione, which is readily available from diphenyl terephthalic acid, via sulfuric acid mediated condensation to provide the corresponding diketone. The diketone can then be reduced to provide the compound of the formula above, wherein R=R'= hydrogen. In general, the reduction of the dione may be effected by utilization of any one of a number of hydride reducing agents, e.g., $NaBH_4$, $LiAlH_4$, and any one of the hydrido type transition metal complexes. $NaBH_4$ is preferred. The compounds of the above formula wherein R and/or R' are $C_1$–$C_6$ hydroxyalkyl residues can be prepared by reacting the tosylate of the compound of formula (1) (i.e., R=R'=p-toluenesulfonyl) with the corresponding diol. For example if the desired compound is R=R'=2-hydroxy-1-yl, the tosylate will be reacted with ethylene glycol.

In the above formula, the term "$C_1$–$C_6$ hydroxyalkyl residues" refers to compounds having from one to six carbon atoms and one free hydroxyl group. Examples include 2-hydroxyeth-1-yl, 3-hydroxyprop-3-yl, 4-hydroxybut-1yl, 5-hydroxypent-1-yl, 6-hydroxyhex-1-yl, and the like. The alkyl portions of such residues are either straight or branched chain alkyl groups.

As noted above, compounds of formula (1) in either cis or trans form or a mixture thereof are useful as monomeric residues in polyesters. Thus as a further aspect of the present invention, there is provided a polyester having from about 2 to about 8 mole percent of residues of a compound of formula (1). The polyesters referred to herein include linear, thermoplastic, crystalline or amorphous polyesters produced by conventional polymerization techniques from one or more diols and one or more dicarboxylic acids. The polyesters normally are molding or fiber grade and have an inherent viscosity (I.V.) of about 0.4 to about 1.2 (dL/g).

Suitable diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, Z,8-bis(hydroxymethyl)-tricyclo-[5.2.1.0]-decane wherein Z represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

Suitable acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedicarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

Preferred polyesters comprise at least about 50 mole percent terephthalic acid residues and at least about 50 mole percent ethylene glycol and/or 1,4-cyclohexanedimethanol residues and about 2 to about 8 mole percent of residues of a compound of formula (1). Particularly preferred polyesters are those containing from about 75 to 100 mole percent terephthalic acid residues and from about 75 to 100 mole percent ethylene glycol residues.

The linear polyesters may be prepared according to polyester forming conditions well known in the art. For example, a mixture of one or more dicarboxylic acids, preferably aromatic dicarboxylic acids, or ester forming derivatives thereof, and one or more diols may be heated in the presence of esterification and/or polyesterification catalysts at temperatures in the range of about 150° to about 300° C., and pressures of atmospheric to about 0.2 mm Hg. Normally, the dicarboxylic acid or derivative thereof is esterified or transesterified with the diol(s) at atmospheric pressure and at a temperature at the lower end of the specified range. Polycondensation then is effected by increasing the temperature and lowering the pressure while excess diol is removed from the mixture.

Typical catalyst or catalyst systems for polyester condensation are well known in the art. For example, catalysts disclosed in U.S. Pat. Nos. 4,025,492; 4,136,089; 4,176,224; 4,238,593; and 4,208,527, incorporated herein by reference, are deemed suitable in this regard. Further, R. E. Wilfong, *Journal of Polymer Science*, 54 385 (1961) sets forth typical catalysts which are useful in polyester condensation reactions. A preferred catalyst system is Mn/Ti/Sb/Co/P.

A preferred temperature range for a polyester condensation is about 260° C. to about 300° C.

The polyester compositions provided herein are useful in the manufacturing of containers or packages for comestibles such as beverages and food. By the use of known heat setting techniques, certain of the polyesters are, in terms of color, I.V. and heat distortion, stable at temperatures up to about 100° C. Such stability characteristics are referred to herein as "hot fill" stability. Articles molded from these polyesters exhibit good thin wall rigidity, excellent clarity and good barrier properties with respect to moisture and atmospheric gases, particularly carbon dioxide and oxygen.

The linear polyesters most preferred for use in articles having "hot fill" stability comprise poly-(ethylene terephthalate), poly(ethylene terephthalate) wherein up to 5 mole percent of the ethylene glycol residues have been replaced with residues derived from 1,4-cyclohexanedimethanol and poly(ethylene 2,6-naphthalenedicarboxylate), wherein the polyesters have been sufficiently heat set and oriented by methods well known in the art to give a desired degree of crystallinity. By definition, a polymer is "hot fill" stable at a prescribed temperature when less than 2% change in volume of a container manufactured therefrom occurs upon filling the same with a liquid at the temperature. For the manufacture of blow molding beverage bottles, the most preferred polyesters have an I.V. of 0.65 to 0.85, and a Tg of >70° C., and film sections cut from the bottle have a Water Vapor Transmission Rate of 1.5 to 2.5 g mils/100 in.$^2$-24 //////////////≧hours, a Carbon Dioxide Permeability of 20 to 30 cc. mils/100 in.$^2$-24 hours-atm., and an Oxygen Permeability of 4 to 8 cc. mils/100 in.$^2$-24 hours-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk River, Minnesota, and the Carbon Dioxide Permeability by the standard operating procedure of a MOCON PERMATRAN C II, also of Modern Controls.

EXPERIMENTAL SECTION

EXAMPLE 1

To a 300 mL flask containing methanol (130 mL), an argon atmosphere, and indeno[1,2-β]fluorene-6,12-dione (13.0 g; 0.046 mole) chilled to 0° C., was added NaBH$_4$ (1.8 g; 0.046 mole) as a solid. The resulting mixture was stirred for 1 h, and allowed to warm to room temperature. An additional 2.5 g of NaBH$_4$ was added until the violet color was discharged. Acetone (10 mL) followed by dilute HCl (50 mL) were added.

The resulting mixture was filtered, and the residue was washed with water and dried in a vacuum. The yield was 10 g. mp 285°-295° C. (dec.) The material was recrystallized from dimethylformamide. Anal. Calc. for C$_{20}$H$_{14}$O$_2$:C,83.92; H, 4.90. Found C, 83.01; H, 4.97. FDMS:m/e 286 (286 calculated). $^1$H NMR (DMSO-d$_6$,δ):7.99 s(1H), 7.82 d(1H), 7.59 d(1H), 7.40 t(1H), 7.31 t(1H), 5.87 d(1H), 5.52 d(1H), 3.35 br(water). All signals had shoulders indicating the compound was a mixture of cis and trans isomers.

EXAMPLE 2

A 19.40 g sample of dimethyl terephthalate, 2.10 g of indeno[1,2-β] fluorene-6,12-diol, 14.40 g of ethylene glycol, and 100 ppm Ti(as tetra isopropyl titanate) were combined and heated at 190° C. under nitrogen for 2 h and allowed to cool. The reaction mixture was then heated at 200° C. under nitrogen for 1 h, followed by an increase to 215° C. and then to 250° C. over the next 2.5 h. A 0.05 mm Hg vacuum was then applied for about 30 minutes. The resulting dark amber crystalline polymer had the following properties.

Inherent viscosity=0.289 dL/g determined at 0.5% weight/volume in 60/40 phenol/tetrachloroethane solution DSC: T$_g$(2nd cycle)=78° C. (Differential Scanning Calorimetry, DuPont Model 912, 20° C./min scan rate)

Tch (2nd cycle)=139° C. (−8.631 cal/g)

Tcc=193° C. (−11.83 cal/g)

Tm=254° C./254° C. (12,32/13.02 cal/g)

Molecular Weight Distribution by Gel Permeation Chromatography in 70/30 methylene chloride/hexaflouroisopropanol Mw=19633 Mz=26387 Mv=18192

Mn=11878 Mz/n=2.2216

Mw/n=1.6530 Mz/MW=1.3440

EXAMPLE 3

A 19.4 g sample of dimethyl terephthalate, 0.75 g sample of indeno[1,2-β] fluorene 6,12-diol, 15.11 g sample of ethylene glycol, and 100ppm Ti(as tetraisopropyl titanate) were reacted in a manner analogous to that described in Example 2 to provide a dark amber crystalline polymer having the following properties: Inherent viscosity=0.439 dL/g T$_g$(2nd cycle)=80° C. Tch(2nd cycle)=149° C. (−7.928 cal/g)

Tcc−175° C.(−9.851 cal/g)

Tm=258°/256°(12.37/10.84 cal/g)

MW=30430 Mz=42789 Mv=27964

Mn=17113 Mz/n=2.5004

Mw/Mn=1.7782 Mz/w=1.4062

We claim:

1. A compound of formula (1)

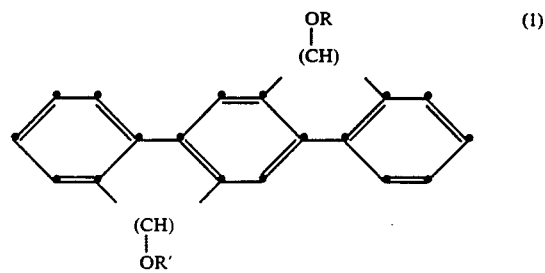

wherein R and R' are independently hydrogen or C$_1$–C$_6$ hydroxyalkyl residues.

2. The compound of claim 1, wherein R=R'=2-hydroxyeth-1-yl.

3. The compound of claim 1, which is indeno[1,2-β] fluorene-6,12-diol.

4. A polyester having from about 2 to about 8 mole percent of residues of the formula

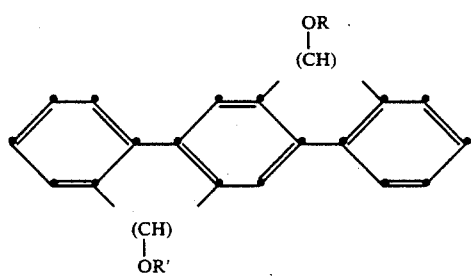

wherein R and R' are independently hydrogen or C$_1$–C$_6$ hydroxyalkyl residues.

5. The polyester of claim 4, wherein R=R'=2-hydroxyeth-1-yl.

6. The polyester of claim 4, wherein the compound of formula 1 is indeno[1,2-β] fluorene 6,12-diol.

7. A polyester comprised of at least about 50 mole percent terephthalic acid residues and at least about 50 mole percent ethylene glycol and/or 1,4-cyclohexanedimethanol residues and about 2 to about 8 mole percent of residues of the formula

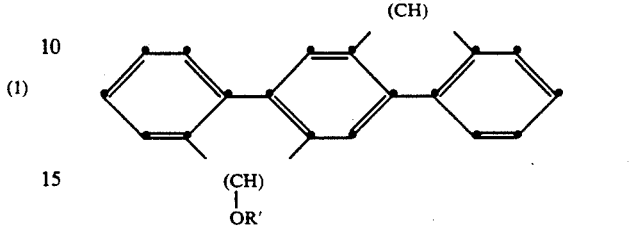

wherein R and R' are independently hydrogen or C$_1$–C$_6$ hydroxyalkyl residues.

8. The polyester of claim 7, wherein R=R'=2-hydroxyeth-1-yl.

9. The polyester of claim 7, wherein the compound of formula (1) is indeno[1,2-β] fluorene-6,12-diol.

10. A shaped or formed article comprised of the polyester of claim 4.

11. A shaped or formed article comprised of the polyester of claim 7.

* * * * *